United States Patent [19]

Patton

[11] Patent Number: 5,005,433
[45] Date of Patent: Apr. 9, 1991

[54] ASBESTOS SAMPLE REMOVAL TOOL

[76] Inventor: Eugene K. Patton, 3000 N. Knoxville, Peoria, Ill. 61603

[21] Appl. No.: 383,031

[22] Filed: Jul. 20, 1989

[51] Int. Cl.⁵ ........................ G01N 1/28; G01N 1/04
[52] U.S. Cl. .................... 73/864.44; 73/863; 73/864.91
[58] Field of Search .......... 73/864.44, 864.45, 864.91, 73/863

[56] References Cited

U.S. PATENT DOCUMENTS

| | | | |
|---|---|---|---|
| 2,664,269 | 12/1953 | Knight et al. | 73/864.44 X |
| 2,881,933 | 4/1959 | Bull | 73/864.44 X |
| 2,987,922 | 6/1961 | Harrington | 73/864.44 |
| 3,125,883 | 3/1964 | Wollner . | |
| 3,444,938 | 11/1967 | Ballmann | 175/173 |
| 3,704,627 | 12/1972 | Beaudoux . | |
| 4,096,749 | 6/1978 | Stewart | 249/DIG. 4 X |
| 4,516,438 | 5/1985 | Hodge | 73/864.44 |
| 4,573,539 | 3/1986 | Carroll et al. | 175/247 X |

FOREIGN PATENT DOCUMENTS

| | | | |
|---|---|---|---|
| 1543043 | 10/1968 | France | 73/864.44 |
| 918090 | 2/1963 | United Kingdom | 73/864.45 |

*Primary Examiner*—Tom Noland
*Attorney, Agent, or Firm*—Arnold, White & Durkee

[57] ABSTRACT

To remove a densely packed insulation sample from a coring bit, a sample removal tool is provided. The sample removal tool holds the coring bit in axial alignment with a plunger rod. The plunger rod moves axially toward the coring bit as a trigger mechanism is repeatedly actuated. Preferably, frictional plates encompass the plunger rod and force the plunger rod into the coring bit. The plunger rod contacts the sample within the coring bit and forces the sample out of the bit. After the sample is removed, the plunger rod is pulled back through the coring bit, and the coring bit is released from the sample removal tool.

20 Claims, 2 Drawing Sheets

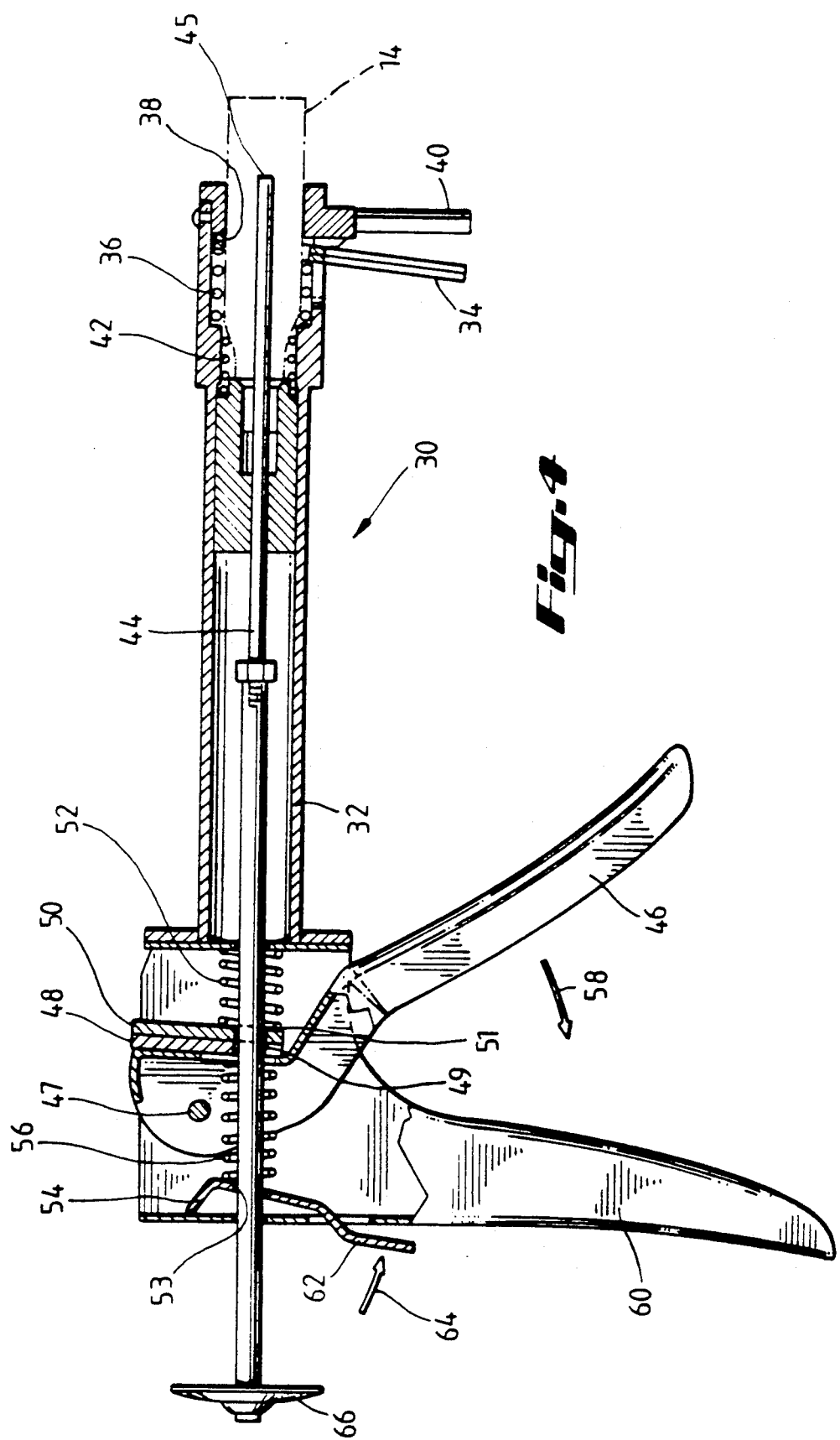

ASBESTOS SAMPLE REMOVAL TOOL

BACKGROUND OF THE INVENTION

1. Field of the Invention

This invention relates generally to asbestos sampling and testing, and more particularly to a tool for removing an asbestos sample from a sampling bit.

2. Description of the Related Art

Until the late 1970's, asbestos was extensively used as a fire-resistant insulation material in buildings. Initially, insulation containing asbestos found particular application around furnace pipes and hot water pipes because of its ability to withstand prolonged exposure to heat. Because of this ability, asbestos also been used in other building products, such as ceiling and wall insulation, and ceiling tile.

However, after the discovery that asbestos fibers cause cancer, particularly lung cancer, asbestos usage in building materials subsided. Moreover, in view of concern over the public welfare, federal laws now mandate the removal of existing asbestos insulation from public buildings. Since literally thousands of buildings across the United States contain asbestos insulation, the progress toward removing all of the existing asbestos insulation is still continuing.

Typically, insulation containing asbestos cannot be readily identified by merely viewing the insulation. Therefore, various types of sampling tools are used to remove a number of samples from insulation throughout each building. One type of sampling tool is commonly referred to as a coring bit. Coring bits vary in diameter and length depending on the type of insulation to be sampled. For best results, the bit should extend through the entire thickness of the sampled insulation, because the insulation may have been manufactured in layers and one of the layers may contain asbestos. A coring bit typically includes a hollow cylindrical portion which is open on at least one end. The open end may be sharpened or it may incorporate a plurality of saw-like teeth so that the bit readily cuts into insulation when pushed or rotated. This cutting action forces the severed insulation into the hollow portion of the bit.

The insulation samples are then tested in a laboratory to determine the amount of asbestos contained in the sample. However, the insulation sample contained within the coring bit is difficult to remove for testing. Sample removal is often accomplished by digging the sample out of the bit with a knife or screwdriver blade while a vise holds the bit. Another removal method used if the coring bit is open at both ends entails pushing the sample out of the bit while a vise holds the bit. Since some insulation is quite densely packed, the aforementioned removal methods can be time consuming, labor intensive and frustrating.

Accordingly, the present invention provides a tool which easily removes an asbestos sample from a coring bit, and which holds the coring bit during removal of the sample.

SUMMARY OF THE INVENTION

In accordance with the present invention there is provided a method and apparatus for removing an asbestos sample from a coring bit. The sample may be taken by various methods, such as by using a coring bit in an appropriate manual sampling tool or electric drill. The coring bit preferably includes a sharp-edged end portion for cutting into a substrate to be sampled, a cylindrical portion which holds the sample, and a tool engagement portion which connects to the appropriate sampling tool. The coring bit is hollow, and further includes a backing disc or wadding which is disposed within the sampling bit between the sample holding portion and the tool engagement portion. The backing disc prevents a portion of the sample from entering the tool engagement portion where the sample could possibly contaminate the sampling tool.

After the sample has been taken, the coring bit is removed from the sampling tool and inserted into a sample removal tool. The sample removal tool of the present invention receives the tool engagement portion of the coring bit, and securingly holds the coring bit with spring-loaded locking washers which encompass the outer periphery of the sampling bit. A trigger-actuated rod, which is adapted to enter the tool engagement portion of the coring bit, forces the backing disc and the sample toward the sharp-edged end portion of the coring bit. After the sample has been ejected the spring-loaded locking washers are actuated so that the coring bit may be removed from the sample removal tool. Additional assistance for removal of the coring bit is provided by a spring which is disposed in the bit receiving portion of the sample removal tool, and which biases the coring bit against the locking washers.

BRIEF DESCRIPTION OF THE DRAWINGS

Other objects and advantages of the invention will become apparent upon reading the following detailed description and upon reference to the drawings in which:

FIG. 4 is a cross-sectional view of the sample removal tool of FIG. 3.

Figure 1:
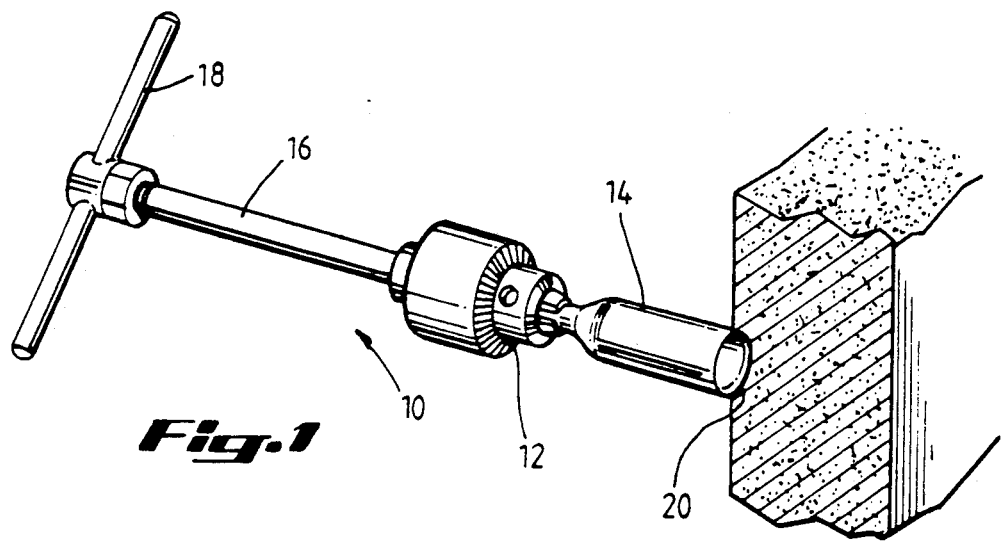
FIG. 1 is perspective view of a sampling tool containing a coring bit.

While the invention is susceptible to various modifications and alternative forms, specific embodiments thereof have been shown by way of example in the drawings and will be described in detail herein. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENT

Referring initially to FIG. 1, a manual sampling tool is generally designated by a reference numeral 10. The sampling tool 10 includes a chuck portion 12 into which the coring bit 14 is inserted prior to obtaining an insulation sample. A T-shaped handle 18 is rigidly attached to the chuck portion 12 via a rod 16, and rotation of the handle 18 causes the coring bit 14 to bite into insulation to be sampled. Therefore, as the coring bit 14 is forced into the insulation, the severed insulation becomes lodged into the coring bit 14.

Figure 2:
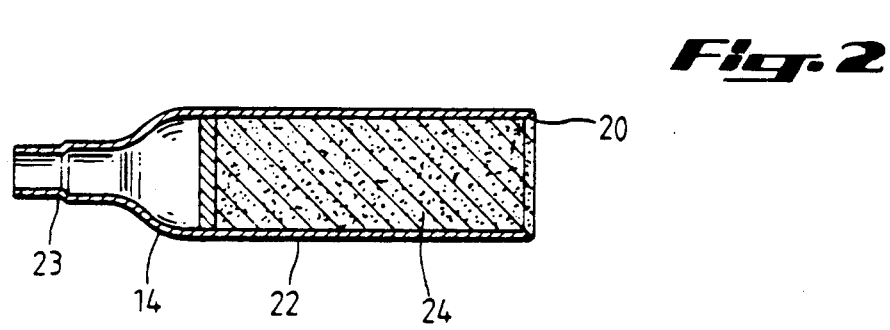
FIG. 2 is a cross-sectional view of the coring bit illustrated in FIG. 2.

To help the coring bit 14 cut into the insulation, the coring bit 14 has a cutting edge 20 as illustrated in FIG. 2. Rotation of the sampling tool 10 causes the cutting edge 20 of the coring bit 14 to sever the insulation in a circular fashion. As shown in FIG. 2, the coring bit 14 has a hollow, generally cylindrical configuration which includes a sample holding body 22 and a shank 23. The chuck portion 12 may be of any type suitable to fixedly hold the shank 23 of the coring bit 14 in the tool 10. As the coring bit 14 moves into the insulation by applying pressure to the handle 18, a sample 24 of the insulation is forced into the body 22 of the coring bit 14. A piece of cardboard or plastic wadding 26 disposed within the sample holding body 22 prevents the insulation sample 24 from entering the shank 23 of the coring bit 14 as the sample is being taken.

Once the sample 24 has been taken, the chuck portion 12 is loosened so that the coring bit 14 may be removed from the sampling tool 10. Then, the sample 24 must be removed from the coring bit 14 for testing. If the coring bit is reusable, the sample is removed in the field. However, if the coring bit is damaged or dull, the coring bit 14 containing the sample 24 is sent to a laboratory where the sample is removed for testing.

Figure 3:
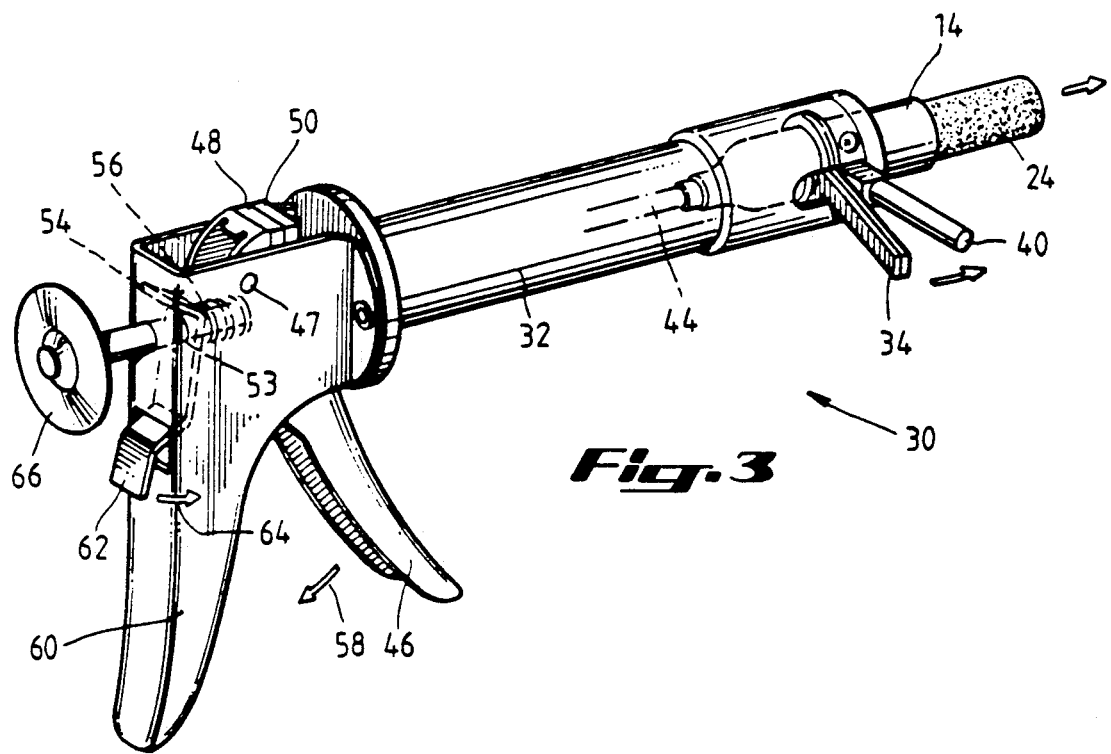
FIG. 3 is perspective view of a sample removal tool in accordance with the present invention.

As illustrated in FIGS. 3 and 4, a sample removing tool is generally designated by a reference numeral 30. The sample removing tool 30 is designed to hold the coring bit 14 while the tool removes the sample from the bit. The tool 30 uses mechanical advantage so that very little effort is expended during the removal of the sample.

The coring bit 14 fits into the open end of a tubular portion 32 of the tool where it is held by a locking washer 34 which is biased by a spring 36. The spring-loaded locking washer 34 encompasses the out periphery of the bit and securingly holds the coring bit 14. To insert a coring bit into the sample removing tool 30, the locking washer 34 is pressed toward a handle 40. In this position, the locking washer 34 depresses the spring 36, and an aperture 38 in the washer 34 becomes aligned with the coring bit 14. The coring bit 14 is inserted into the aperture 38 until a spring 42 mounted inside of the tube 32 is compressed. Then, the locking washer 34 is released so that the spring 36 presses the inner surface of the locking washer 34 which forms the aperture 38 against the outer shell of the coring bit 14. In this position, the locking washer 34 holds the coring bit 14 within the tube 32 against the bias of the spring 42.

Once the coring bit 14 is secured within the tool 30, the sample 24 is forced out of the coring bit 14 by a plunger 44 which has an end 45 adapted to pass within the hollow shank of the coring bit 14. A trigger 46 is pivotally secured within the tool 30 by a rod 47, and actuates the plunger 44 using a rachet mechanism. The trigger 46 pushes a pair of friction plates 48,50 against the plunger 44 which extends through apertures 49,51 in the friction plates 48,50. The friction plates 48,50 are biased against an upper portion of the trigger 46 by a spring 52. On the other side of the upper portion of the trigger 46, the plunger 44 extends through an aperture 53 in a releasing plate 54 which is biased against the upper portion of the trigger 46 by a spring 56.

To move the plunger 44 toward the coring bit 14, the trigger 46 is moved in the direction of the arrow 58 toward a handle 60. The trigger movement compresses both springs 52 and 56 and slightly tilts the friction plates 48,50 so that the inner surfaces which form the apertures 49,51 frictionally engage the plunger 44. As the trigger 46 pushes the friction plates 48,50 toward the tube 32, the plunger 44 moves toward the coring bit 14 by virtue of the frictional engagement with the plates 48,50. When the trigger 46 is released, the springs 52,56 bias the trigger into its original position. The releasing plate 54 retains the plunger 44 in its new position because the inner surface of the releasing plate 54 which forms the aperture 53 is frictionally engaged with the plunger 44.

After the trigger 46 has been actuated a few times, the end 45 of the plunger 44 enters the coring bit 14 through the shank 16 and contacts the wadding 26. Further actuation of the trigger 46 causes the plunger 44 to push the wadding 26, and thus the sample 24, toward the cutting edge 20 of the coring bit 14. Preferably, the plunger 44 is long enough to extend beyond the end of the inserted coring bit 14 to ensure that all of the sample 24 is easily removed.

After the sample 24 has been pushed out of the coring bit 14, a lever 62 on the releasing plate 54 is pressed in the direction of arrow 64. In this position, the aperture 53 in the releasing plate 54 is aligned with the plunger 44 so that the releasing plate is no longer in frictional engagement with the plunger and, therefore, the plunger 44 may be pulled back through the tube 32. A disc 66 is attached to the end of the plunger 44 so that the plunger 44 can be easily pulled. The coring bit 14 is then released from the tube 32 by once again depressing the locking washer 34 toward the handle 40 so that the spring 42 catapults the coring bit 14 from the tube.

What is claimed is:

1. A method for removing an insulation sample from a hollow coring bit, comprising the steps of:
   inserting said coring bit containing said insulation sample in a bit receiving portion of a sample removal tool, said tool being adapted to securingly hold said coring bit in axial alignment with a rod;
   actuating a rachet mechanism of said sample removal tool which forces said rod axially toward said coring bit; and
   forcing said insulation sample out of said coring bit by repeatedly actuating said rachet mechanism to force said rod through the hollow of said coring bit.

2. The method, as set forth in claim 1, wherein said coring bit is securingly held in alignment with said rod by a spring-loaded locking washer which encompasses said coring bit.

3. The method, as set forth in claim 1, further comprising he step of:
   withdrawing said rod from said coring bit after said sample has been removed.

4. The method, as set forth in claim 3, further comprising the step of:
   releasing said coring bit from said bit receiving portion of said tool.

5. The method, as set forth in claim 4, wherein said step of releasing includes ejecting said coring bit from said bit receiving portion of said tool by a spring disposed within said bit receiving portion of said tool.

6. A method for removing an insulation sample from a hollow coring bit, comprising the steps of:
   inserting said coring bit containing said insulation sample in a bit receiving portion of a sample removal tool, said tool being adapted to securingly hold said coring bit in axial alignment with a rod;
   actuating a rachet mechanism of said sample removal tool which forces said rod axially toward said coring bit,
   said rachet mechanism comprising a friction plate having an aperture therein through which said rod is positioned, said friction plate having a first position wherein said aperture is aligned with said rod to allow said rod to slide axially within said aperture and a second position wherein said friction plate frictionally engages said rod; and a trigger pivotally mounted in said tubular member, and being adapted to engage and move said friction plate between said first and second positions, wherein movement of said friction plate from said first position to said second position causes said rod to slide axially toward said coring bit and wherein repeated actuation of said trigger causes said rod to enter said coring bit and force said sample from said coring bit; and forcing said insulation sample out of said coring bit by repeatedly actuating said rachet mechanism to force said rod through the hollow of said coring bit.

7. An apparatus for removing an insulation sample from a coring bit, comprising:

a tubular member with opposing ends having a handle on one end thereof;

means for holding said coring bit in the opposite end of said tubular member from said handle;

a plunger adapted to move axially within said tubular member, said plunger having one end which is adapted to enter said coring bit;

a trigger pivotally mounted in said handle and being moveable from a first position to a second position;

a rachet mechanism connecting said plunger to said trigger, said rachet mechanism being adapted to force said plunger axially toward said coring bit in response to moving said trigger from said first position to said second position, and wherein repeated actuation of said trigger causes said one end of said plunger to enter said coring bit and force said sample from said coring bit.

8. The apparatus, as set forth in claim 7, wherein said holding means includes a spring-loaded locking washer which encompasses said coring bit.

9. The apparatus, as set forth in claim 8, wherein said locking washer securingly holds said coring bit in alignment with said rod.

10. The apparatus, as set forth in claim 7, wherein said rachet mechanism includes:

a friction plate having an aperture therein through which said rod is positioned, said friction plate having a first position wherein said aperture is aligned with said rod to allow said rod to slide axially within said aperture and a second position wherein said friction plate frictionally engages said rod, wherein said trigger is adapted to engage and move said friction plate between said first and second positions, so that movement of said friction plate from said first position to said second position causes said rod to slide axially toward said coring bit.

11. The apparatus, as set forth in claim 7, further comprising:

means for withdrawing said rod from said coring bit after said sample has been removed.

12. The apparatus, as set forth in claim 7, further comprising:

means for releasing said coring bit from said holding means.

13. The apparatus, as set forth in claim 12, wherein said releasing means includes:

a spring disposed within said opposite end of said tubular member which ejects said coring bit from said opposite end of said tubular member upon release of said holding means.

14. A tool for removing an insulation sample from a coring bit, comprising:

a tubular member with opposing ends having a handle on one end thereof;

means for holding said coring bit in the opposite end of said tubular from said handle;

a plunger adapted to move axially within said tubular member, said plunger having one end which is adapted to enter said coring bit;

a friction plate having an aperture therein through which said plunger is positioned, said friction plate having a first position wherein said aperture is aligned with said plunger to allow said plunger to slide axially within said aperture and a second position wherein said friction plate frictionally engages said plunger;

a trigger pivotally mounted in said tubular member, and being adapted to engage and move said friction plate between said first and second positions, wherein movement of said friction plate from said first position to said second position causes said plunger to slide axially toward said coring bit and wherein repeated actuation of said trigger causes said plunger to enter said coring bit and force said sample from said coring bit.

15. The apparatus, as set forth in claim 14, wherein said holding means includes a spring-loaded locking washer which encompasses said coring bit.

16. The apparatus, as set forth in claim 15, wherein said locking washer securingly holds said coring bit in alignment with said rod.

17. The apparatus, as set forth in claim 14, further comprising:

means for withdrawing said rod from said coring bit after said sample has been removed.

18. The apparatus, as set forth in claim 17, wherein said withdrawing means includes:

a releasing plate having an aperture therein through which said plunger is disposed, said releasing plate being movable between a first position wherein said releasing plate frictionally engages said plunger and a second position wherein said releasing plate allows said plunger to slide axially within said aperture.

19. The apparatus, as set forth in claim 14, further comprising:

means for releasing said coring bit from said holding means.

20. The apparatus, as set forth in claim 19, wherein said releasing means includes:

a spring disposed within said opposite end of said tubular member which ejects said coring bit from said opposite end of said tubular member upon release of said holding means.

* * * * *